United States Patent [19]

Molinoff

[11] Patent Number: 4,917,674
[45] Date of Patent: Apr. 17, 1990

[54] MOUTH MOISTURIZING DEVICE

[76] Inventor: Henry C. Molinoff, 234 Edgewood Ave., Smithtown, N.Y. 11787

[21] Appl. No.: 273,839

[22] Filed: Nov. 21, 1988

Related U.S. Application Data

[63] Continuation-in-part of Ser. No. 148,087, Apr. 4, 1988, Pat. No. 4,838,882.

[51] Int. Cl.<sup>4</sup> .................................................. A61M 31/00
[52] U.S. Cl. ........................................ 604/286; 128/859; 604/54; 604/904
[58] Field of Search ............... 433/168.1; 604/48, 54, 55, 93, 94, 285, 286, 304, 305, 904, 286, 294, 303, 904; 128/112.1, 114.1, 830, 833, 834, 839, 859, 860, 861, 832, 887, 893, 894, 899

[56] References Cited

U.S. PATENT DOCUMENTS

| | | | |
|---|---|---|---|
| D. 33,764 | 12/1900 | Georges | 128/894 |
| 271,625 | 2/1883 | Goff | 604/904 |
| 335,799 | 2/1886 | Darby | 604/305 |
| 688,446 | 12/1901 | Stempel | 604/304 |
| 689,808 | 12/1901 | Johnson | 604/379 |
| 1,275,127 | 8/1918 | Campbell | 604/294 |
| 1,732,697 | 10/1929 | Ryan | 604/286 |
| 1,804,670 | 5/1931 | Brennan | 128/48 |
| 1,932,383 | 10/1933 | Richardson | 604/904 |
| 2,081,715 | 5/1937 | Scholl | 128/894 |
| 2,098,340 | 11/1937 | Henahan | 128/859 |
| 2,146,985 | 2/1939 | Robell | 604/904 |
| 2,178,704 | 11/1939 | Robinson | 604/904 |
| 2,286,817 | 6/1942 | Knight | 604/904 |
| 2,343,157 | 2/1944 | Quering | 604/303 |
| 2,393,446 | 1/1946 | Schlumbohm | 604/309 |
| 2,464,310 | 3/1949 | Harwood | 604/904 |
| 2,493,416 | 1/1950 | Negri | 604/286 |
| 2,664,631 | 1/1954 | Hollander et al. | 433/168.1 |
| 2,725,054 | 11/1955 | Harpel | 128/163 |
| 3,037,506 | 6/1962 | Penksa | 604/904 |
| 3,055,369 | 9/1962 | Graham, Jr. | 604/904 |
| 3,150,662 | 9/1964 | Carlson, Jr. et al. | 604/55 |
| 3,226,826 | 1/1966 | Town | 433/168.1 |
| 3,397,695 | 8/1968 | Voss | 604/904 |
| 3,429,308 | 2/1969 | Russell | 604/54 |
| 3,536,074 | 10/1970 | Alfred | 604/93 |
| 3,570,489 | 3/1971 | Brown | 604/286 |
| 3,777,754 | 12/1973 | Plachy | 604/308 |
| 3,886,935 | 6/1975 | Sprague | 128/57 |
| 3,965,905 | 6/1976 | Schoenholz et al. | 604/904 |
| 4,020,844 | 5/1977 | Vickery | 604/54 |
| 4,108,180 | 8/1978 | Moehrle | 604/904 |
| 4,202,098 | 5/1980 | Russo | 433/168.1 |
| 4,239,043 | 12/1980 | Gellert | 604/372 |
| 4,341,214 | 7/1982 | Fries et al. | 604/904 |
| 4,360,013 | 11/1982 | Barrows | 604/55 |
| 4,369,773 | 1/1983 | Chvapil | 604/55 |
| 4,553,965 | 11/1985 | Conn et al. | 604/904 |
| 4,564,362 | 1/1986 | Burnhill | 604/55 |
| 4,624,668 | 11/1986 | Siegers | 604/904 |
| 4,678,466 | 7/1987 | Rosenwald | 604/285 |
| 4,692,143 | 9/1987 | Gero . | |
| 4,778,457 | 10/1988 | York | 604/294 |

FOREIGN PATENT DOCUMENTS

| | | | |
|---|---|---|---|
| 0493411 | 3/1950 | Fed. Rep. of Germany | 604/904 |
| 0805662 | 5/1951 | Fed. Rep. of Germany | 604/904 |

Primary Examiner—C. Fred Rosenbaum
Assistant Examiner—Sharon Rose

[57] ABSTRACT

The mouth moisturizing device for treatment of an individual suffering from xerostomia comprises two mouth moisturizing pads, each of which include at least two approximately oval shaped sponge sections placed adjacent each other of a size such that together the sponge sections just fit in a cheek pouch of the individual being treated and an envelope or covering made of knit cotton cloth in which the sponge sections are held, and a connecting strap attached to both of the mouth moisturizing pads. A method of treatment of xerostomia and associated sleep disorders is also described.

4 Claims, 1 Drawing Sheet

MOUTH MOISTURIZING DEVICE

This is a continuation-in-part of application Ser. No. 148,087, filed Apr. 4, 1988 now U.S. Pat. No. 4,838,882.

THE FIELD OF THE INVENTION

My invention relates to a device providing a slow release of moisture in the mouth and to a method for treatment of xerostomia or dry mouth and associated sleep disorders in elderly individuals. Reference should also be made to a copending applications, A MOUTH MOISTURIZING PAD, Ser. No. 148,087.

THE BACKGROUND OF THE INVENTION

A dry mouth is often associated with medication, particularly heart drugs. Dry mouth is also the result of oral surgery for a malignancy, especially involving an X-Ray treatment. It may be caused by chronic sinusitis and its attendant post-nasal drip. Furthermore it is a common complaint of no known etiology of elderly individuals.

The persistence of a dry mouth at night can disturb sleep causing the individual suffering from it to waken frequently, even every hour. Furthermore peridontal disease and increased tooth decay as well as loss of teeth can be a result of xerostomia.

Current treatment has consisted of room humidifiers, and drugs, chiefly pilocarpine. Also patients with dry mouth are advised to drink water, rinse their mouth with fluids such as mouth wash, chew gum or suck hard candy. These latter suggestions of course can only be followed when the patient is awake and are impossible to perform when asleep. Room humidifiers and drugs have unfortunately proven largely ineffective.

THE OBJECTS OF THE INVENTION

It is an object of my invention to provide an improved method for treating xerostomia or dry mouth which can act effectively even while the individual suffering from xerostomia sleeps without danger to the individual.

It is another object of my invention to provide an improved safe treatment for xerostomia which does not involve use of medication which is taken internally.

It is an additional object of my invention to provide a safe device which is inserted in the mouth which is effective in the treatment of xerostomia even when the individual suffering from xerostomia sleeps.

It is a further object of my invention to provide a safe device for treating a sleep disorder including frequent nocturnal awakening which is the result of xerostomia.

SUMMARY OF THE INVENTION

According to my invention a method for treating an individual suffering from xerostomia comprises treating, advantageously saturating, a mouth moisturizing pad, which is of a size approximately equal to but not significantly less than the size of the cheek pouch of the individual suffering from xerostomia, with water and inserting it in a cheek pouch in the mouth of the individual. Advantageously the moisture content of the mouth moisturing pad is periodically replenished as necessary by sipping water and holding the water in the vicinity of the mouth moisturizing pad in the mouth.

This treatment is completely effective providing a slow release of moisture analogous to what occurs in an uneffected individual when the tissues of and glands in the mouth release saliva. Furthermore the treatment for xerostomia proceeds effectively during sleep so that the associated sleep disorder involving frequent awakening is alleviated. Thus an elderly individual who needs a good night sleep, particularly a heart patient, is provided with a means of getting that good sleep.

The mouth moisturizing device according to my invention comprises two mouth moisturizing pads, each including at least two sponge portions positioned adjacent each other which together are approximately equal to but not significantly less than the size of the cheek pouch of the individual being treated and an envelope or covering made of cloth which covers both of the two sponge portions and holds them together, and a connecting strap which holds the two mouth moisturizing pads together of a length such that each mouth moisturizing pad can comfortably reside in a cheek pouch of the individual. This mouth moisturizing device is particularly safe since when both mouth moisturizing pads are in their respective cheek pouches it is less likely to be dislodged inadvertently than a single mouth moisturizing pad. The connecting strap can press against the teeth.

Advantageously the sponge portions are made of a polyester foam for durability and resiliency. Knit cotton cloth may be used for the envelope or covering for durability as well as comfort. Of course a porous or water permeable covering material must be used.

The dimensions of each mouth moisturizing pad are critical since it is to be used while an individual is sleeping. It must not be too large so that it is evident by making the individual uncomfortable. On the other hand if it were too small its effectiveness would be decreased and, more importantly, it could be swallowed or inadvertently drawn in the bronchial tubes.

The mouth moisturizing pad is advantageously made of two sections of polyester sponge so that the pad does not become lumpy as water is drawn from it when it is adjacent the teeth in the mouth. The outer sponge section takes the shape of the cheek while the interior sponge section can be deformed. It is also desirable that their outer surfaces be somewhat convex so that they fit the shape of the cheek pouch. The two sections provide desirable additional comfort for the user.

A single mouth moisturizing pad however can be inserted in one cheek pouch although this provides less water capacity and is less safe than using two pads attached by the connecting strap. Nevertheless since the one pad fits the cheek pouch it is very unlikely that it will be dislodged even during sleep.

BRIEF DESCRIPTION OF THE DRAWING FIGURES

SPECIFIC DESCRIPTION

Figure 1:
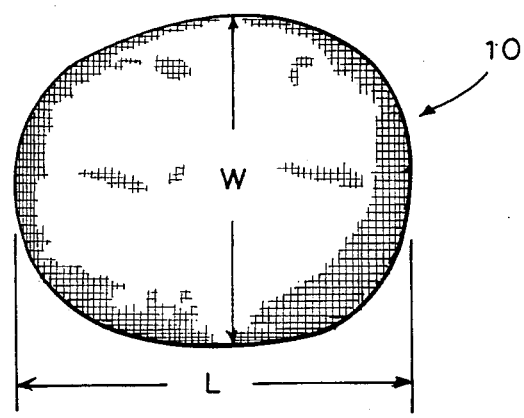
FIG. 1 is a side elevational view of a mouth moisturizing pad of my invention.
Figure 2:
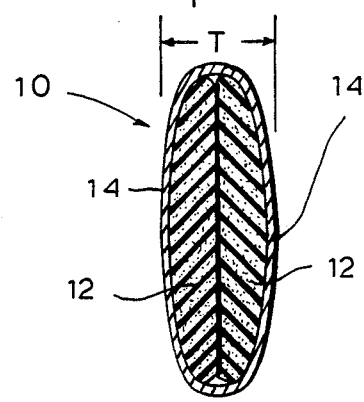
FIG. 2 is a cross sectional view of the mouth moisturizing pad of FIG. 1.

The mouth moisturizing pad 10 shown in the FIG. 1 comprises two oval polyester sponge sections 12 placed side by side in an envelope or covering 14 made if knit cotton cloth. The polyester sponge sections 12 are place together and knit cotton cloth pieces are placed around these sponge sections 12 and attached together, especially by sewing, to form the envelop or covering 14. Of course the covering or envelope 14 completely surrounds and encloses the sponge sections as shown in FIGS. 1 and 2 of the drawing.

The size of the mouth moisturizing pad 10 is critical and should be about the size of the cheek pouch of the individual using it, i.e. a length, l, of about 6 cm and a width, w, of about 3 and ½ cm varying about 1 cm from these dimensions according to the individual. The thickness, t, is advantageously about 2 cm. If it is too large, it is uncomfortable but if it is too small it can be swallowed or caught in the bronchial tubes or its moisture content needs to be replaced too often.

Figure 3:
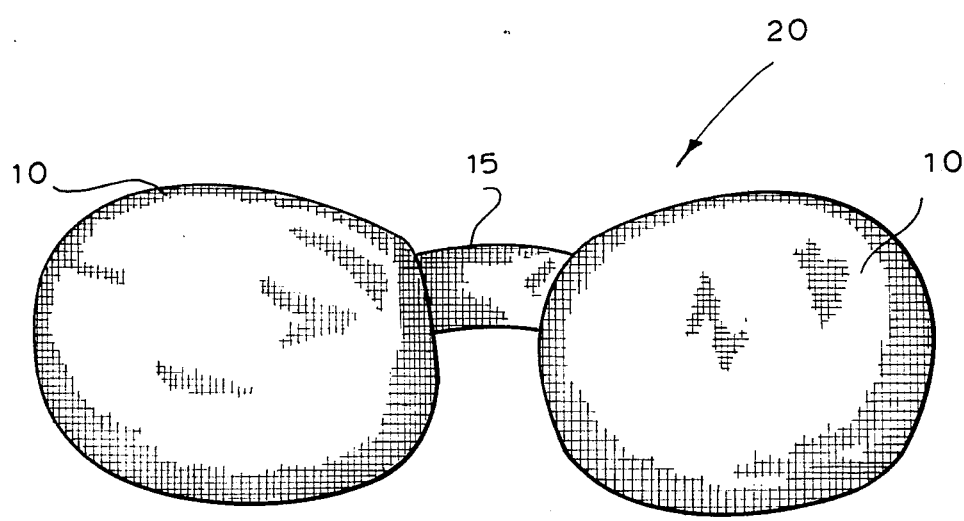
FIG. 3 is a partially cutaway side elevational view of the mouth moisturizing device according to my invention.

The mouth moisturizing device 20 according to my invention is shown in FIG. 3 and comprises two mouth moisturizing pads 10 which are attached together by a cotton strap 15. The length of this connecting strap 15 is such that each mouth moisturizing pad 10 can comfortably reside in a cheek pouch of the individual. The connecting strap 15 is placed against the teeth and helps prevent the moisturizing pads 10 from straying from the cheek pouches, especially during sleep.

By "cheek pouch" we mean the space between the closed teeth and the inside surface of the cheek. Further my invention is not intended to be limited to the details provide above and it will be understood that various omissions, modifications, substitutions and changes in the forms and details of the device illustrated in the drawing and in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of the prior art, fairly constitute essential characteristics of the generic or specific aspects of this invention.

What is claimed is new and what is desired to be protected by Letters Patent is set forth in the following claims:

1. A medical device for safe treatment of an individual suffering from xerostomia comprising two mouth moisturizing pads, each of which hold at least one sponge section and have a covering made of cloth in which said sponge section is held, said pad having dimensions which are approximately equal to but not significantly less than those of a cheek pouch of said individual, and further comprising a connecting strap attached to each of said mouth moisturizing pads of a length such that each of said mouth moisturizing pads can comfortably reside in one of said cheek pouches of said individual while said strap is supported at least partially by the teeth of said individual, said sponge section being saturable with water for gradual dispensing of said water in the mouth and containing a portion of said water.

2. A medical device according to claim 1 in which said portion of said water saturates said sponge section.

3. A medical device according to claim 2 in which said covering completely encloses and surrounds said sponge section.

4. A medical device according to claim 2 in which said sponge sections are oval and are made of polyester foam.

* * * * *